United States Patent [19]

Yaginuma et al.

[11] Patent Number: 4,732,910
[45] Date of Patent: Mar. 22, 1988

[54] ENZYME INHIBITING SUBSTANCE

[75] Inventors: Satoshi Yaginuma; Akira Asahi; Masaki Takada; Mitsuo Hayashi; Kiyofumi Fukukawa, all of Shizuoka, Japan

[73] Assignee: Toyo Jozo Co, Ltd., Japan

[21] Appl. No.: 843,003

[22] Filed: Mar. 24, 1986

[30] Foreign Application Priority Data

Mar. 26, 1985 [JP] Japan .................................. 60-59439
Jan. 23, 1986 [JP] Japan .................................. 61-10982

[51] Int. Cl.$^4$ .................. A61K 31/355; C07D 303/48
[52] U.S. Cl. ..................................... 514/475; 549/549
[58] Field of Search ......................... 549/549; 514/475

[56] References Cited

U.S. PATENT DOCUMENTS

| | | | |
|---|---|---|---|
| 4,333,879 | 6/1982 | Tamai et al. | 549/549 |
| 4,387,238 | 6/1983 | Goi et al. | 549/549 |
| 4,393,228 | 7/1983 | Sawada et al. | 549/549 |
| 4,418,075 | 11/1983 | Tamai et al. | 549/549 |
| 4,479,937 | 10/1984 | Sato et al. | |

OTHER PUBLICATIONS

Carl R. Noller, "Chemistry of Organic Compounds", (1965), W. B. Saunders Company, p. 439.
W. H. Johnson et al., J. Chem. Soc., (C), (1971), pp. 748–753.
99Agric. Biol. Chem., 42, (3), 523–536, 1978.
The Journal of Antibiotics, 25, 263–266, 1972.
Abstracts of J55035012; J54141795; J52031024; J54141734; J54141737; J54141750.

Primary Examiner—Norma S. Milestone
Attorney, Agent, or Firm—Antonelli, Terry and Wands

[57] ABSTRACT

A substance is provided which has strong enzyme inhibitory activity against thiol proteases such as papain, ficin, bromelain, etc. and which is represented by the following formula:

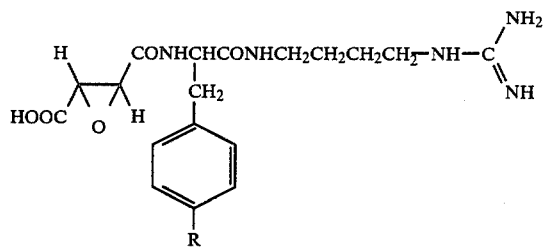

(wherein R is a hydrogen atom or a hydroxyl group), its pharmaceutically acceptable salt or hydrate.

2 Claims, 5 Drawing Figures

ENZYME INHIBITING SUBSTANCE

This invention relates to a substance represented by the formula:

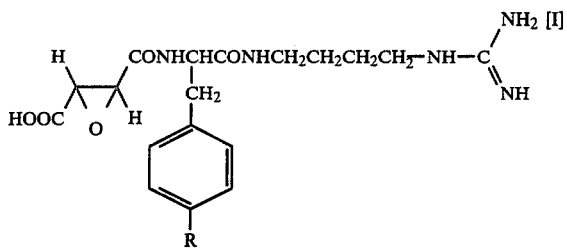

wherein R is a hydrogen atom or a hydroxyl group, a pharmaceutically acceptable salt or hydrate thereof and a process for producing same.

This novel substance is useful at least as medicines or reagents for researches which have enzyme inhibitory activity.

Hitherto, it has been known that thiol protease inhibitors have anti-inflammatory activity. Thiol protease inhibitors known are urinary proteins (Japanese Patent Unexamined Publication No. 155324/84), E-64 (Agric. Biol. Chem 42, 523–528, 1978), Antipain (J. Antibiot. 25, 263–266, 1972), epoxide compounds (Japanese Patent Unexamined Publication Nos. 153778/80, 115878/80, 47668/80, 35012/80, 141750/79, 141737/79, 141795/79, 141734/79, 108948/78, 108936/78, 108923/78 and 31024/77) and the like.

The E-64 above, for example, is a substance isolated from culture of Aspergillus japonicus TPR 64 strain, and furthermore is prepared by the processes, i.e., (1) a process which comprises subjecting N-carbobenzyloxy-1,4-diaminobutane carbonate ("carbobenzyloxy" will be abbreviated to "CBZ" hereinafter) as a starting material to addition of nitroguanidyl, elimination of CBZ, condensation with butyloxycarbonyl-L-leucine succinimide ester (which will be abbreviated to "Boc-L-Leu-OSu" hereinafter), eliminations of Boc and nitro groups, condensation with ethyl hydrogen transepoxysuccinic acid and hydrolysis; and (2) a process which comprises subjecting N-CBZ-1,4-diaminobutane carbonate as a starting material to condensation with Boc-L-Leu-OSu, elimination of Boc group, condensation with ethyl hydrogen trans-epoxysuccinic acid, elimination of CBZ, addition of nitroguanidyl, hydrolysis, and elimination of nitro group (Agric. Biol. Chem., 42(3), 529–536, 1978). However, the process (1) above referred to has the drawbacks that preparation of the starting material of N-CBZ-1,4-diaminobutane carbonate is difficult and that fat-solubility is lost during the synthesis procedure due to elimination of nitro group which is a protective group for guanidyl group and thus difficulty is encountered when purification is made. The process (2) above has also the drawbacks that the preparation of the starting material is difficult as in the process (1) and besides the reaction for introduction of nitroguanidyl group carried out in the later stage accompanies a large amount of by-products and yield is very small.

After searches for novel physiologically active substances produced by microorganisms, the inventors have succeeded in isolating the substance of this invention represented by the above formula [I] from cultured medium of a microorganism belonging to Myceliophthora newly separated from soils. The substance is found to be physiologically active and has a strong enzymatic inhibitory activity against thiol protease such as papain, ficin, bromelain, etc.

The substance of this invention represented by the formula [I] has been concluded to be novel from the facts that this substance is higher in enzyme inhibitory activity than the known substances and that, on the basis of physicochemical and biological properties, there are no natural nor chemically synthesized compounds same in chemical structure or properties as the substance of this invention. This substance is named "Estatin". Furthermore, the substance of the formula [I] where the group R is a hydrogen atom is named "Estatin A" and the substance of R being a hydroxyl group "Estatin B".

In the accompanying drawings.

Estatin A and Estatin B of the present invention may be expected to have uses for medicines and reagents for researches. The Estatin A and Estatin B are possibly effective for treatment of inflammation, muscle dystrophy, etc., because they can strongly inhibit thiol proteases such as papain which have thiol group which participates in development of physiological activity, calcium-dependent neutral thiol proteases, etc. Furthermore, Estatin A and Estatin B possibly have anti-allergic activity, because they can not inhibit production of IgG antibodies but of IgE antibodies which participate in allergic diseases.

| Physicochemical properties and biological properties of Estatin (Estatin A and Estatin B) | | |
|---|---|---|
| (1) Physicochemical properties | Estatin A | Estatin B |
| (a) Appearance | White needle crystal | White needle crystal |
| (b) Neutral, acidic or basic | Basic substance | Basic substance |
| (c) Elementary analysis | Found: C = 52.8%, H = 6.37%, N = 17.40% Calcd. for $C_{18}H_{25}N_5O_5 \cdot H_2O$ C = 52.80%, H = 6.65%, N = 17.10% | Found: C = 50.93%, H = 6.49%, N = 16.73% Calcd. for $C_{18}H_{25}N_5O_6 \cdot H_2O$ C = 50.82%, H = 6.40%, N = 16.46% |
| (d) Molecular formula | $C_{18}H_{25}N_5O_5$ | $C_{18}H_{25}N_5O_6$ |
| (e) Molecular weight (from FAB mass spectrum) | 391 | 407 |
| (f) Specific rotatory power $[\alpha]_D^{24}$ | | |

| | Product | | |
|---|---|---|---|
| $[\alpha]_D$ | Estatin A (Epoxy moiety in DL-form) | Estatin A (L-form) | Estatin B (L-form) |
| Product by fermentation process | | +41.8 ± 5° (C: 0.6, H₂O) | +46.8 ± 5° (C: 0.2, 0.1 NHCl) |
| Product by synthetic | −30.90 ± 5° (C: 0.77, | +47.37 ± 5° (C: 0.61, H₂O) | +45.25 ± 5° (C: 0.137, |

-continued

| Physicochemical properties and biological properties of Estatin (Estatin A and Estatin B) | |
|---|---|
| process 0.1 NHCl) | 0.1 NHCl) |

(g) Ultraviolet absorption spectrum

Figure 1:
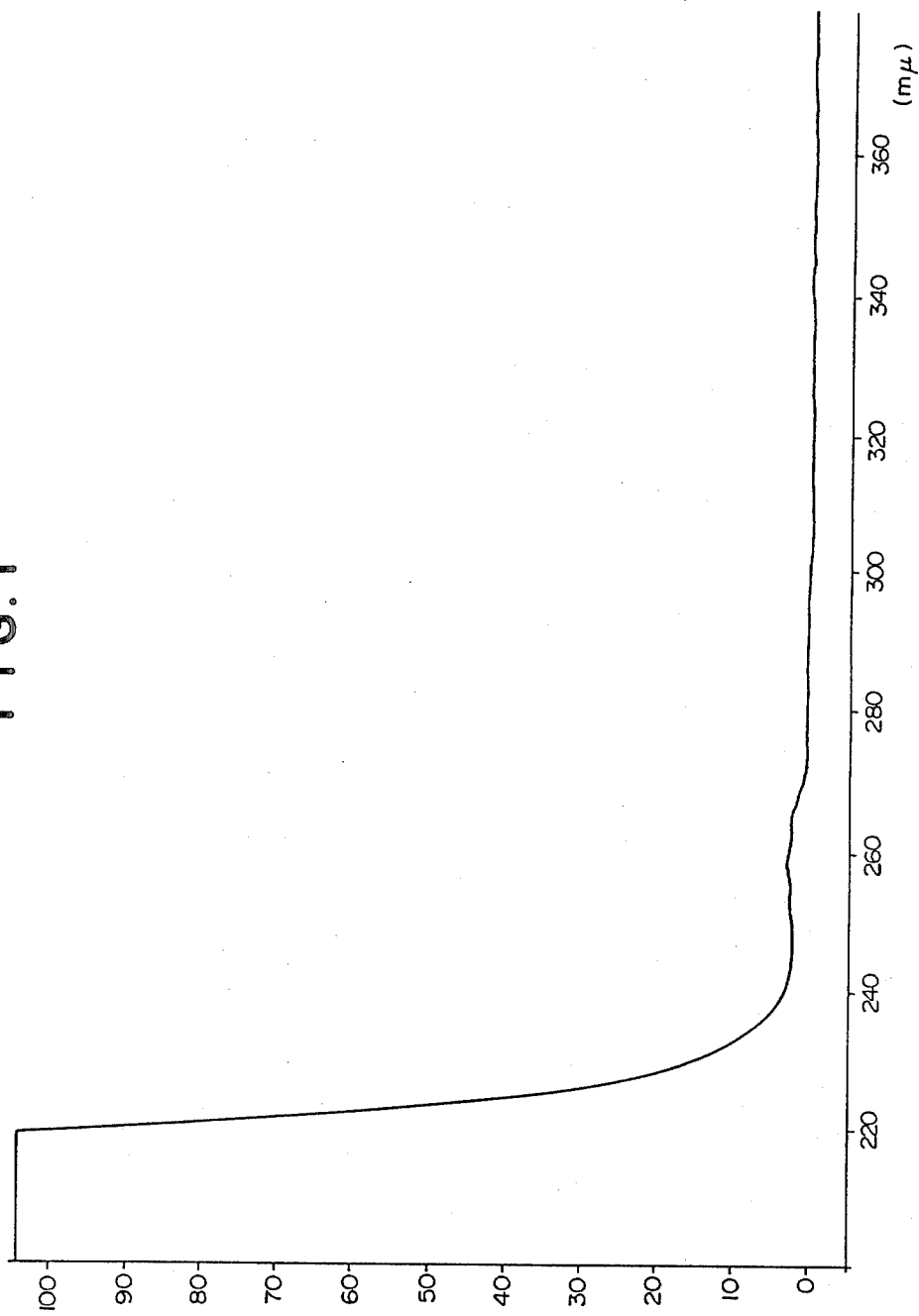
FIG. 1 shows an ultraviolet absorption spectrum of Estatin A in water.
Figure 2:
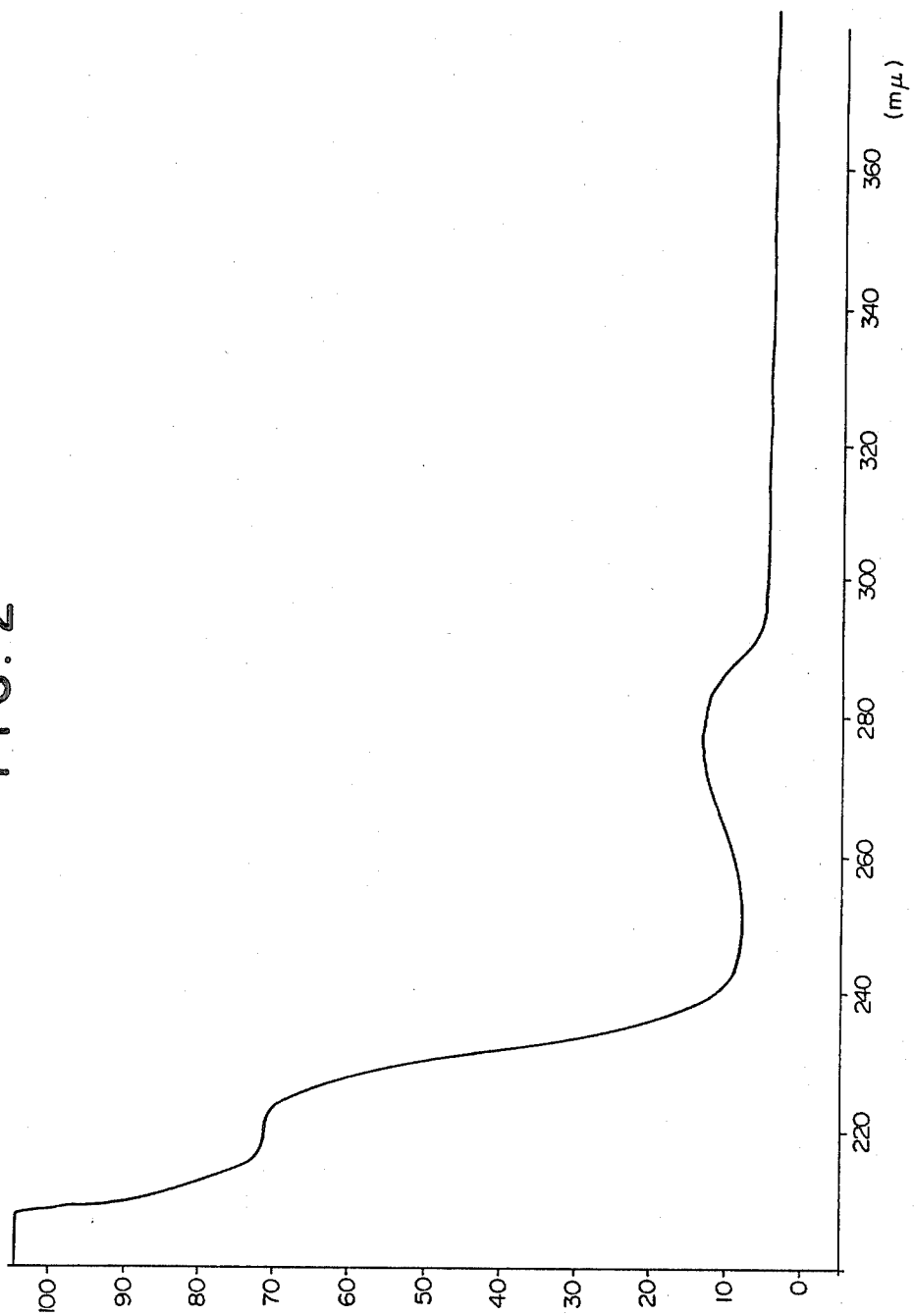
FIG. 2 shows an ultraviolet absorption spectrum of Estatin B in water.

Ultraviolet absorption spectra of Estatin A and Estatin B in aqueous solutions are shown in FIG. 1 and FIG. 2, respectively. Results for Estatin A are as follows:

$\lambda_{max}^{H2O}$ ($E_{1\ cm}^{1\%}$) 247 m$\mu$ (4.1), 0.252 m$\mu$ (4.6), 259 m$\mu$ (5.1), 0.264 m$\mu$ (4.1), 269 m$\mu$ (2.2).

Results for Estatin B are as follows:

$\lambda_{max}^{H2O}$ ($E_{1\ cm}^{1\%}$) 222 m$\mu$ (274.1), 276 m$\mu$ (38.3), 283 m$\mu$ (31.8).

(h) IR absorption spectra

Figure 3:
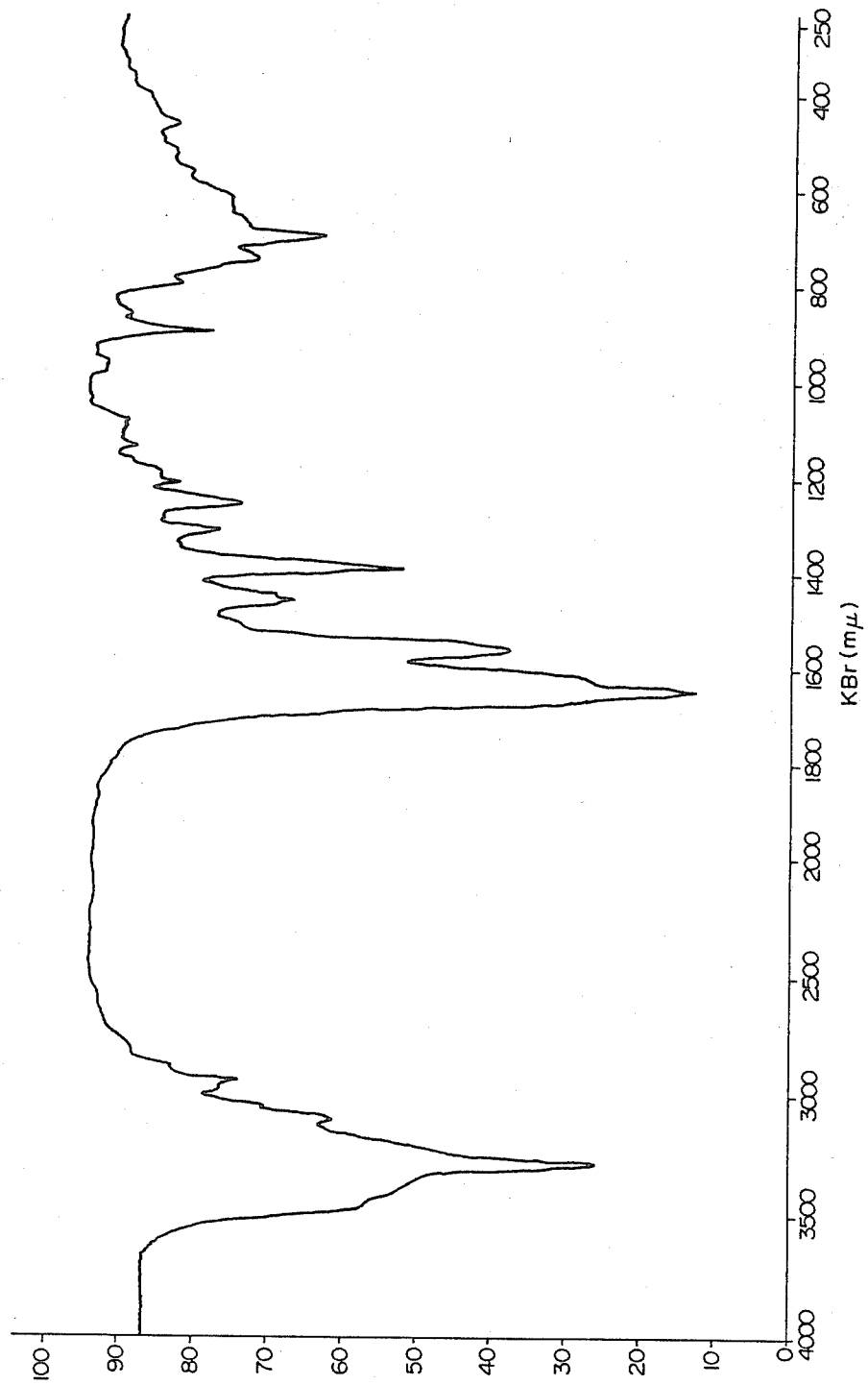
FIG. 3 shows an infrared absorption spectrum of Estatin A.
Figure 4:
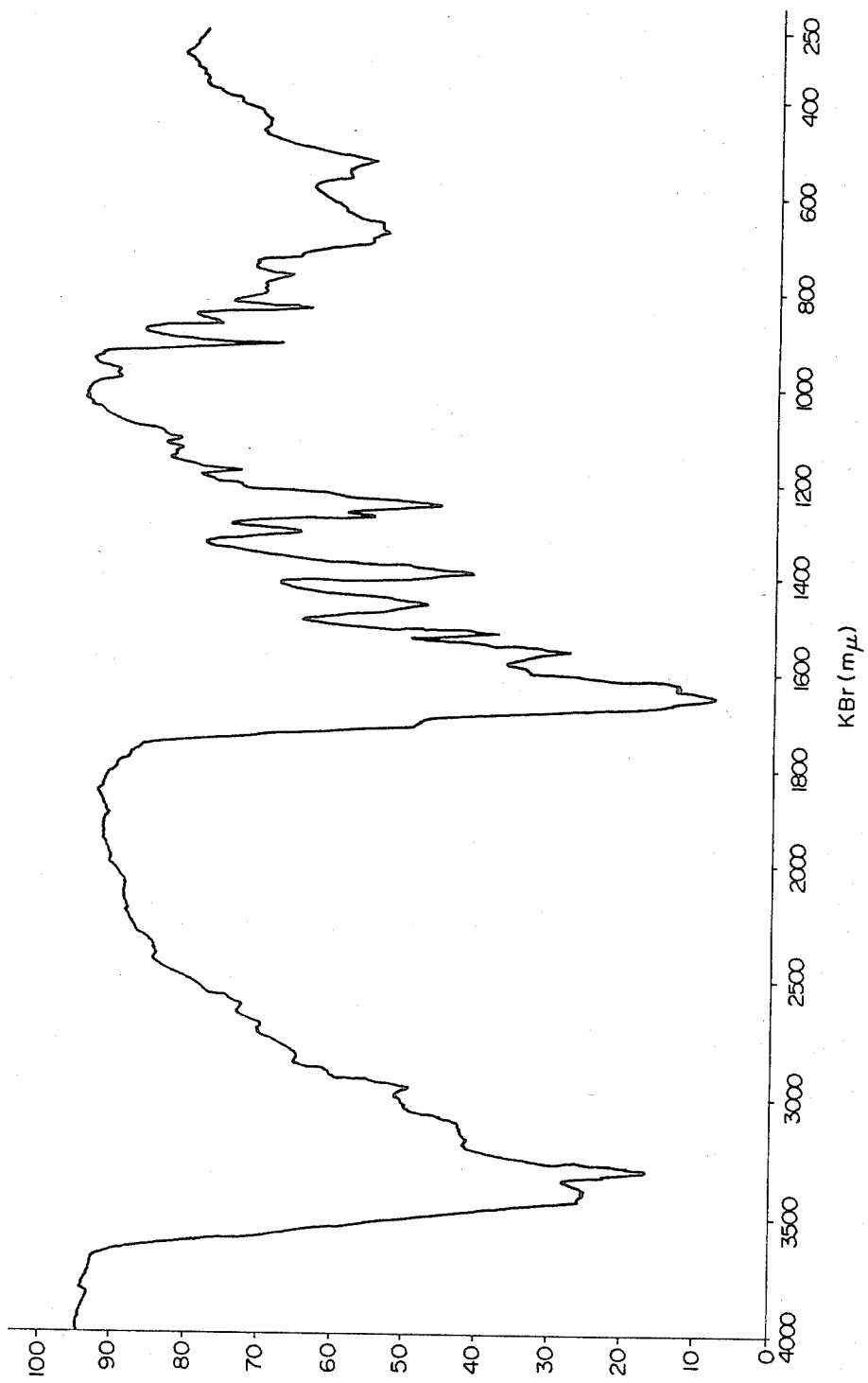
FIG. 4 shows an infrared absorption spectrum of Estatin B.
Figure 5:
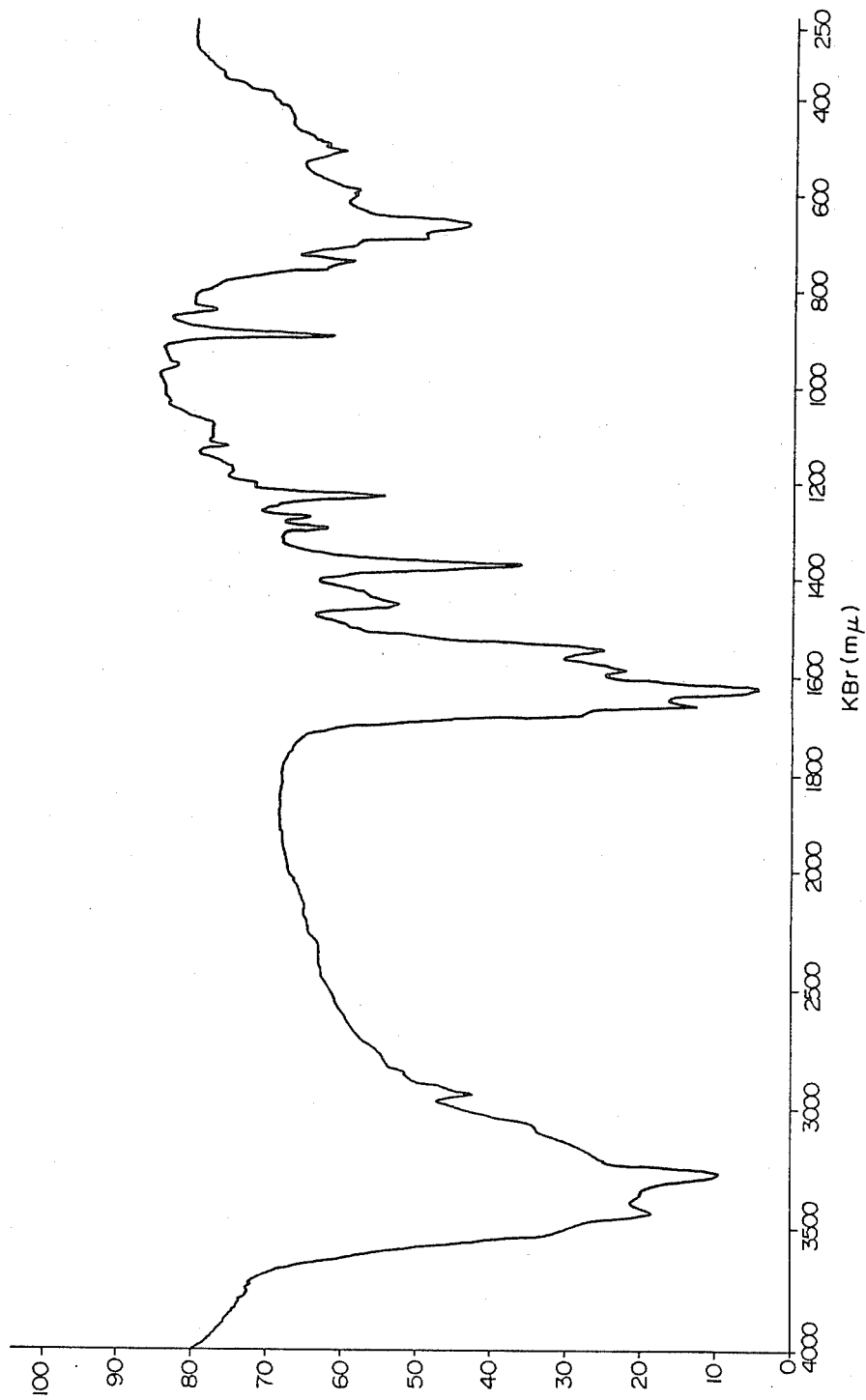
FIG. 5 shows an infrared absorption spectrum of Estatin A wherein the epoxy moiety is in DL-form.

IR absorption spectra of Estatin A and Estatin B by KBr method are shown in FIG. 3, FIG. 4 and FIG. 5, respectively.

Estatin A: Characteristic absorption bands at 3260, 1640, 1550, 1440, 1380, 1250 and 900 cm$^{-1}$.

Estatin B: Characteristic absorption bands at 3280, 1650, 1550, 1520, 1460, 1400, 1300, 1250 and 900 cm$^{-1}$.

(i) PMR spectra

Chemical shift, proton number and multiplicity of Estatin A measured in heavy water by 100 MHz PROTON NMR (internal standard DSS) are as follows:

1.37 ppm (m, 4H)
3.09 ppm (m, 6H)
3.24 ppm (d, J=2.1, 1H)
3.51 ppm (d, J=2.1, 1H)
4.53 ppm (t, J=7.9, 1H)
7.33 ppm (m, 5H)

Chemical shift, proton number and multiplicity of Estatin B measured in heavy water with heavy hydrochloric acid by 100 MHz proton NMR (internal standard DSS) are as follows:

| | |
|---|---|
| 1.33 ppm (m, 4H) | 6.85 ppm (d, J=8.3, 2H) |
| 3.05 ppm (m, 6H) | 7.14 ppm (d, J=8.3, 2H) |
| 3.52 ppm (d, J=2.0, 1H) | |
| 3.76 ppm (d, J=2.0, 1H) | |
| 4.50 ppm (t, J=8.0, 1H) | |

(j) C-13 NMR spectra

Chemical shift and multiplicity of Estatin A measured in heavy water at 25 MHz (internal standard dioxane; 67.4 ppm) are as follows:

| | | | |
|---|---|---|---|
| 25.9 ppm(t) | 53.6 ppm(d) | 129.6 ppm(d) | 170.1 ppm(s) |
| 26.2 ppm(t) | 55.2 ppm(d) | 130.0 ppm(d) | 173.1 ppm(s) |
| 37.8 ppm(t) | 56.1 ppm(d) | 130.0 ppm(d) | 174.2 ppm(s) |
| 39.4 ppm(t) | 128.0 ppm(d) | 136.9 ppm(s) | |
| 41.5 ppm(t) | 129.6 ppm(d) | 157.3 ppm(s) | |

Chemical shift and multiplicity of Estatin B measured in heavy water with heavy hydrochloric acid added thereto at 25 MHz (internal standard dioxane; 67.4 ppm) are as follows:

| | | | |
|---|---|---|---|
| 25.9 ppm(t) | 53.0 ppm(d) | 128.6 ppm(s) | 168.5 ppm(s) |
| 26.2 ppm(t) | 54.1 ppm(d) | 131.4 ppm(d) | 171.1 ppm(s) |
| 37.1 ppm(t) | 56.3 ppm(d) | 131.4 ppm(d) | 173.0 ppm(s) |
| 39.6 ppm(t) | 116.3 ppm(d) | 155.3 ppm(s) | |
| 41.6 ppm(t) | 116.3 ppm(d) | 157.4 ppm(s) | |

| | Estatin A | Estatin B |
|---|---|---|
| (k) Solubility | Soluble in water, acetic acid, dimethyl sulfoxide and pyridine. Insoluble in benzene, chloroform, ethyl acetate and petroleum ether. | Soluble in water, acetic acid, dimethyl sulfoxide and pyridine. Insoluble in benzene, chloroform, ethyl acetate and petroleum ether. |
| (l) Color reaction | Estatin A Positive in decoloring reaction of potassium permanganate and Sakaguchi reaction and negative in ninhydrin reaction, Molisch reaction and ferric chloride reaction | Estatin B Positive in decoloring reaction of potassium permanganate and Sakaguchi reaction and negative in ninhydrin reaction, Molisch reaction and ferric chloride reaction. |
| (m) Hydrolysis | Estatin A After hydrolysis with 6N HCl at 105° C. for 18 hours under tight seal, measurement was made by aminoacid automatic analytical device. L-Phenylalanine | Estatin B After hydrolysis with 6N HCl at 105° C. for 18 hours under tight seal, measurement was made by aminoacid automatic analytical device. L-Tyrosine |
| (n) Rf value (by Silica gel f manufactured by Tokyo Kasei Co.) | | |
| Developing solvent | Estatin A | Estatin B |
| Chloroform:methanol:14% ammonia water (20:30:3) | Rf = 0.33 | Rf = 0.22 |
| Chloroform:methanol:water (3:7:1) | Rf = 0.62 | Rf = 0.53 |
| Ethyl acetate:methanol:water (3:5:2) | Rf = 0.65 | Rf = 0.56 |
| Acetonitrile:water (8:2) | Rf = 0.14 | Rf = 0.09 |
| (o) Stability | Estatin A Stable at a pH of 2-9 | Estatin B Stable at a pH of 2-9 |
| (p) Hydrate or pharmaceutically acceptable salt | | |

Estatin A and Estatin B of this invention may be formed as monohydrates. Furthermore, they may form salts with inorganic acids such as hydrochloric acid sulfuric acid and the like or organic acids such as acetic acid, citric acid, tartaric acid and the like or bases such as sodium hydroxide, potassium hydroxide and the like.

For formation of the salts, for example, to a solution containing Estatin A or Estatin B is added said acid or base to carry out reaction, thereby to form a salt, which is recovered.

(2) Biological properties (1) Enzyme inhibitory activity

Enzyme inhibitory activities of Estatin A and Estatin B are shown below.

| Enzymes | Amount of enzyme used (Amount of protein $\mu$g) | Substrate | IC$_{50}$ concentration ($\mu$g/ml) | |
|---|---|---|---|---|
| | | | Estatin A | Estatin B |
| Papain | 60 | Casein | 0.026 | 0.027 |
| Ficin | 60 | Casein | 0.039 | 0.041 |
| Bromelain | 100 | Casein | 0.145 | 0.145 |
| $\alpha$-Chymotrypsin | 200 | Casein | >50 | >50 |
| Trypsin | 1000 | Casein | >50 | >50 |
| Pepsin | 100 | Casein | >50 | >50 |

IC$_{50}$ of synthesized Estatin A whose epoxy moiety is in DL-form for papain inhibitory activity was 0.029 $\mu$g/ml, which was similar to the activity of Estatin A in L-form.

The enzyme reactions were all measured according to the prescribed methods.

($\alpha$-chymotrypsin and pepsin used are those manufactured by PL Biochemical Co., and trypsin is that manufactured by Wako Junyaku Co.)

Estatin A and Estatin B specifically inhibit the activity of thiol proteases such as papain, ficin, bromelain, etc. whose thiol groups participate in development of activity without inhibiting the casein hydrolyzing activity of serine protease represented by trypsin and acid proteases represented by pepsin.

Assay test of the present substance is effected, for example, by Sakaguchi's coloring reaction on decoloring reaction of potassium permanaganate, taking advantage of anti-papain activity, silica gel T.L.C., etc.

One of test methods for estatin of this invention is as follows.

The present Estatin A and Estatin B have anti-papain activity. Quantitative determination is possible based on this activity. The activity can also be utilized for extraction, purification and isolation of Estatin A and Estatin B from culture solution. Method for the quantitative determination will be explained below.

The 0.2 ml of a solution of papain (300 µg/ml, Boeringer Mannheim AG), 0.25 ml of 40 mM cysteine solution dissolved in 5 mM EDTA solution adjusted pH to 6.8 with sodium hydroxide and 0.55 ml of the 50 mM phosphate buffer (pH 6.8) with or without inhibitor were mixed and incubated at 40° C. for 10 min., followed by adding 4 ml of 1.5% casein solution dissolved in a 50 mM phosphate buffer (pH 6.8) to carry out a reaction at 40° C. for 15 min. Then, 2 ml of 1.1M trichloroacetic acid is added to terminate the reaction. After being left to stand at room temperature for one hour, the reaction mixture is centrifuged at 3500 rpm for 10 minutes and absorbance (S) of the trichloroacetic acid soluble fraction at 280 mµ is measured. Similarly, absorbance (B) at 280 mµ is measured when no inhibitors are added. The percent inhibition was calculated by the following formula:

% inhibition = 100 $(B-S)/B$

The amount of inhibitor for 50% inhibition was expressed as $IC_{50}$.

Inhibitory activities against ficin (protein amount: 60 µg, manufactured by Boehringer Mannheim AG) and bromelain (protein content: 100 µg, manufactured by Boehringer Mannheim AG) are also measured by the similar method.

(2) Activity on the production of IgE and IgG antibodies in mice

Activity on the production of IgE antibody was examined by the following method.

Estatin A or Estatin B dissolved in physiological saline were administered ip to $BDF_1$ strain male mice weighing 18-22 g (one group 5 mice) at a dose of 200 mg/Kg. Control group (10 mice) received only physiological saline. After 2 hours from the administration, 4 mg of aluminum hydroxide together with 10 µg of egg albumin was administered ip to immunize them. After 14 days from the immunization, blood was collected and IgE antibody titer was assayed by PCA reaction (See "International Archives of Allergy and Applied Immunology" Vol. 48, Page 16, 1975.).

That is, serum samples were serially diluted and injected intradermally into the back of Wistar strain male rats weighing 200-250 g. After 48 hours, 1 ml of 1% Evans blue in physiological saline containing 2 mg of egg albumin was administered iv and rats were killed 30 min. later, and blueing of saline were observed. PCA titers were expressed on the reciprocal of the maximum dilution which showed definite positive blueing. The results are shown below.

| Test drugs | PCA Antibody TITERS IgE antibody titers | | |
|---|---|---|---|
| Estatin A | <100 <100 | <100 <100 | <100 |
| Estatin B | <100 <100 | <100 100 | <100 |
| Control | 400 800 1600 3200 | 800 800 1600 | 800 800 1600 |

Activity on the production of IgG antibody was examined by the following method.

Estatin A or Estatin B were administered ip to $BDF_1$ strain male mice weighing 18-22 g (one group 5 mice) at a dose of 200 mg/Kg. Control group (10 mice) received only physiological saline.

After 2 hours from the administration each mouse was immunized by intradermal injection with 0.2 mg/0.1 ml of egg albumin together with equal volume of Freund complete adjuvant into the 2 separate sites of the back of the mice. After 2 weeks blood was collected and antibody titers were determined by passive hemagglutination test using glutalaldehyde as coupling reajent. The results are shown below.

| Test drugs | IgG antibody titers | | |
|---|---|---|---|
| Estatin A | 12800, 12800, | 6450, 12800 | 25600 |
| Estatin B | 6400, 25000, | 25600, 12800 | 12800 |
| Control | 12800, 25600, 25600, 12800, 6450 12800, 12800, 12800, 12800, 12800 | | |

That is, Estatin A and Estatin B inhibit the production of IgE antibody which causes allergic diseases, but do not inhibit the production of IgG antibody which pertains in normal immune reaction.

(3) Acute toxicity

Estatin A and Estatin B showed no toxic effect when they were administered ip into mice at a dose of 400 mg/Kg.

(4) Administration method and dose

Estatin of this invention (Estatin A and Estatin B) may be administered in any form of oral agents, injections and rectum suppositories.

Injections may be prepared by adding to estatin a pH regulator, a buffer, stabilizer and a filler and freeze-drying the mixture according to the conventional method. Further, subcutaneous, intramuscular and intravenous injections may be prepared by conventional method with addition of a pH regulator, a buffer, a stabilizer, an isotonic agent and a local anesthetic agent.

Solid preparations for oral administration may be produced by adding to estatin a filler and, if necessary, a binder, a disintegrator, a lubricant, a colorant, taste and smell correctives and then forming the mixture into tablets, coating tablets, granules, powders, capsules, etc. by the conventional method. Liquid preparations for oral administration may be produced by adding to the compound a taste corrective, a stabilizer, a buffer, a smell corrective, etc. and forming therefrom a syrup and a dry syrup by the conventional method.

Rectum suppositories may be prepared by adding to estatin a filler and, if necessary, a surfactant and then making suppositories therefrom by the conventional method.

Dose of estatin varies depending on the condition of patients and the purpose of treatment, but for adults there may be administered 10–1000 mg/once in terms of estatin thrice a day.

The present compound is produced by a microbiological process or by synthesis.

I. Microbiological process

Mycological properties of strain, M4323 used for production of Estatin A and Estatin B are as follows:

(1) State of growth on various media (1) Czapek's agar culture medium

Growth is fast at 30° C. to reach 48–50 mm in diameter but is slow at 26° C. to reach 7–13 mm in diameter after seven days. Colony is flat and velvet-like and becomes powdery with formation of conidia. The margin is somewhat arachnoid. The surface has brownish orange (6C4). Neither release of exudation nor diffusible pigment. The reverse has brownish organe (6C4).

(2) Malt extract agar culture medium

Growth is very fast at 30° C. to reach to cover the whole surface of a Petri dish of 85 mm inner diameter before seven days and 35–45 mm at 26° C. Colony is flat, but is slightly fluffy with formation of aerial hyphae. It becomes powdery with formation of conidia. The margin is somewhat arachnoid. Color of the surface is greyish orange (6B3). Neither exudation nor diffusible pigment is released. The reverse is greyish yellow (4B5).

(3) Potato dextrose agar medium

Growth is very fast at 30° C. to reach 65–67 mm but is slow at 26° C. to reach 11–12 mm after seven days. Colony is flat and velvet-like and becomes powdery with formation of conidia. The margin is somewhat arachnoid. Color of the surface is brownish orange (6C4). Neither exudation nor diffusible pigment is released. The reverse is light brown (5D5).

(2) Physiological properties

| PH range where strain can grow | 2.4–8.2 |
| Optimum pH range for growing | 5.0–7.5 |
| Temperature where strain can grow | 25–49° C. |
| Optimum growing temperature | 37–43° C. |

(3) Morphological characteristics under microscope

Aerial hyphae and substrate hyphae which are vegetative hyphae are different in size. The aerial hyphae are 1–3 μm in diameter and colorless and have smooth wall. The substrate hyphae grow up to 5.5 μm in diameter.

Conidia are formed by blastospore formation. Conidia are formed either directly from aerial hyphae or at the tips of short conidium forming cells. Sometimes one to four conidia are formed from a cell which swells in the form of an ampule. The conidia do not form chains and are in the form of inverted egg or pear of 4.5–10×2–.5–5.5 μm and colorless or light yellowish brown and have walls of smooth surface or slightly rough surface and comprise single cell.

(4) Source from which the strain is isolated and identification and deposition of the strain.

The strain is a fungus isolated from soil of a flower bed in Iriomote island, Okinawa prefecture in Japan. The strain does not propagate sexually but forms conidia. Hyphae have septa. Thus, they belong to imperfect fungi. Conidia formation is blastospore formation and no or short conidiophores are formed. The conidia are formed directly from hyphae or form ampule-like cells and are composed of single cell.

From these characteristics, the strain is identified as belonging to Myceliophthora. There is the genus Chrysosporium which is near the genus Myceliophthora. These genera are distinguishable from each other in that the latter form blastospores while the former form arthrospores or aleuriospores. There are eight species in this genus, but the present strain is identified as *Myceliophthora thermphila* from the characteristics that it forms colonies of nearly brown color, has a high optimum growth temperature of 37°–43° C. and is thermophilic fungus and forms light yellowish brown conidia and is named *Myceliophthora thermophila* M 4323. This strain has been deposited bearing FERM-BP No. 979 at Fermentation Research Institute Agency of Science & Technology, Japan. Indication of colors hereinabove is based on Kornerup. A., and J. H. Wanscher. 1978. "Methuen handbook of colour". 3rd., Eyre Metheun, London.

The identification of strain has been made referring to the following literatures:

van Arx, J. A., 1981. The Genera of Fungi Sporulating in Pure Culture, 424 pp. J. Cramer.

van Oorschot, C. A. N., 1977. The genus Myceliophthora, Persoonia 9: 401–408.

Culturing conditions for production of Estatin of this invention are generally about 30° C. and 3–7 days.

Examples of culture media used in this invention are as follows:

Any media may be used which are suitable for growth of fungi and which can produce Estatin. As examples of carbon sources, mention may be made of saccharides such as glucose, furactose, maltose, sucrose, lactose, galactose, dextrin, starch, glycerine, sorbitol, etc. and vegetable oils such as soybean oil, etc.

As examples of nitrogen source, mention may be made of peptone, yeast extract, meat extract, casein, soybean powder, cotton seed powder, CSL, malt extract, amino acids, urea, ammonium salts, ammonium nitrates, etc.

Furthermore, there may be optionally added minor nutrients such as inorganic salts, e.g. phosphate, chloride or carbonate of potassium, calcium, magnesium, sodium, iron, manganese, cobalt, zinc, etc. and vitamins, e.g., vitamin B, calcium pantothenate, etc.

The culturing may be effected on a solid medium, but usually in liquid medium with shaking or aeration agitating.

Estatin A and Estatin B may be collected, for example, by the following means.

The substances are mainly present in culture filtrate. They are collected high yields by subjecting the filtrate from which the cells have been removed to adsorption on an adsorbent and desorption therefrom. As the adsorbent, there may be used activated charcoal, non-ionic adsorbing resins, ion-exchange resins, etc. For example, Estatin is adsorbed on activated charcoal and eluted with a 50% acetone solution. It may also be adsorbed on Amberlite IR-120B (H+ type) and eluted with ammonia water.

Purification can be effected by combination of the usual means to separate and purify an organic substance, such as adsorption chromatography with silica gel, activated alumina, activated charcoal, non-ionic adsorbing resin or the like, ion-exchange chromatography with ion-exchange resin or the like, partition chromatography with cellulose or the like, gel-filtration with gel-filtration carrier, reversed phase chromatography with alkyl group-bonding silica gel and the like.

More specifically, a crude substance is passed through a column packed with adsorbents such as silica gel, alumina, etc. to adsorb the substance thereto, which is then eluted with a mixed solvent such as ethyl acetate:methanol:water, chloroform:methanol:water, acetonitrile:water, or the like. Desalting, removal of silica gel, etc. may also be carried out by gel-filtration method with Sephadex G-15.

II. Synthetic method

According to this synthetic method, it is possible to produce in large amounts of optically active Estatin A and Estatin B as well as natural products. This will be of great use for evaluation of physiological activities hereafter and this is further expected to lead to commercial production. Furthermore, the synthetic method is made it possible to synthesize Estatin analogs.

One of the methods for synthetic production of Estatin will be shown below.

(1) Synthesis of

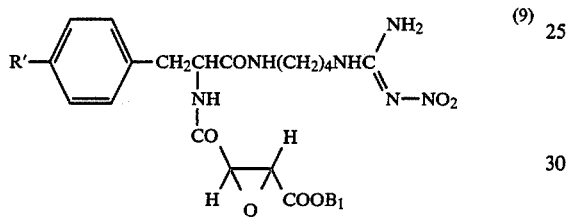

(wherein R' is a hydrogen atom or a hydroxyl group protected with a protective group removable by catalytic reduction such as a benzyl group which may have nucleus substituent including, e.g., benzyl and p-nitrobenzyl groups and $B_1$ is an ester residue removable by saponification such as lower alkyl group, e.g., methyl or ethyl group or an ester residue which may have nucleus substituent and is able to remove by catalytic reduction such as benzyl or p-nitrobenzyl group).

The above compound is afforded by the following method.

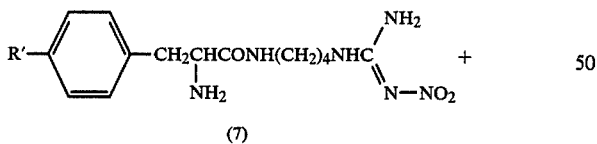

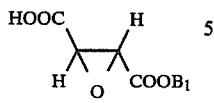

The above reaction is carried out in a solvent such as dimethylformamide by addition of diethyl phosphorocyanidate and triethylamine. The DL-form of compound (8) is commercially available. L- or D-form may be produced by the disclosed method of K. Mori et al "Tetrahedron" 36, 87 (1980).

(2) synthesis of

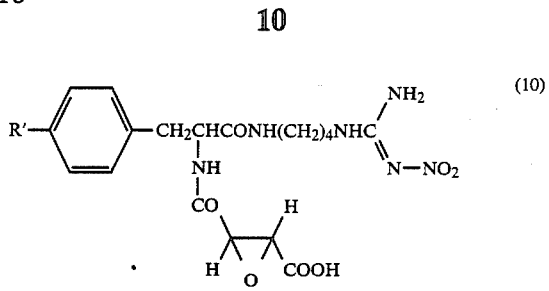

The above compound may be obtained by saponification of the compound (9) having an ester residue removable by saponification with 1-1.1 equivalent of KOH in methanol. Reaction period is 3 hours. NaOH may be used in place of KOH.

(3) Synthesis of

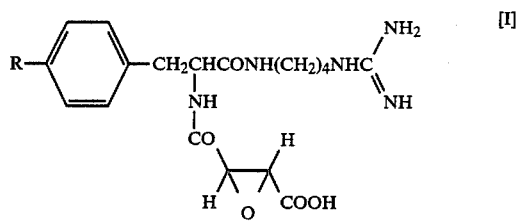

The compound of the formula (10) or the compound (9) having an ester residue removable by catalytic reduction is dissolved in methanol, acetic acid and water, and the solution is catalytically reduced with hydrogen in the presence of a palladium on carbon to give the titled compound. Reaction time is 10-15 hours. Platinum or platinum on carbon may also be used.

In the present synthetic procedure mentioned above, the nitro group, protecting group for guanidyl of agmatine residue, is left unremoved until final step. Thus, purification by silica gel is easy besides yield is increased.

(4) For reference, synthesis of the compound (7) will be shown below.

(1) Synthesis of

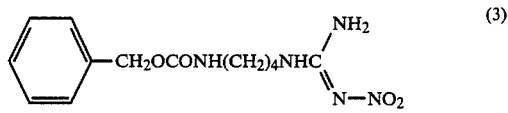

This compound is obtained by the following reaction.

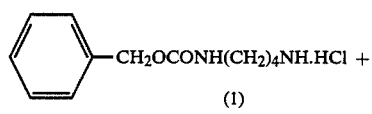

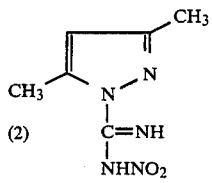

The compound (1) is dissolved in 1.1 equivalent of the compound (2) in a lower alcohol such as ethanol and triethyl amine is added thereto. The mixture is refluxed for 3 hours. The compound (1) is commercially available.

(2) Synthesis of

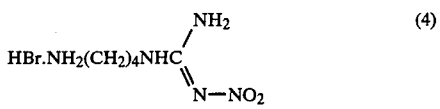

This compound is obtained by deblocking of the compound (3) with a 25% acetic acid solution of HBr at room temperature for 30 minutes. HF or Na—NH₃ may be used instead of HBr.

(3) Synthesis of

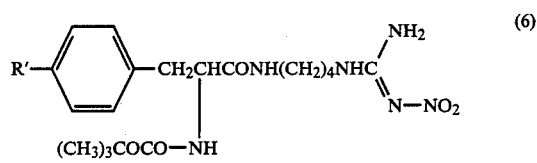

This compound can be produced by the following reaction.

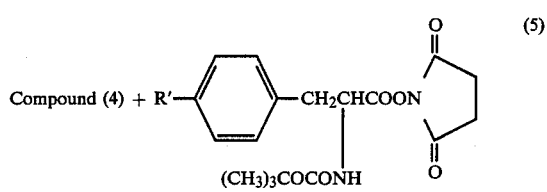

This reaction is effected using the compounds in equal molar ratio at room temperature for 2–6 hours in 1,2-dimethoxyethane.

(4) Synthesis of the compound of the compound (7)

The titled compound is obtained by the deblocking of the compound (6) with 99% formic acid at room temperature for 2 hours. Acids such as HCl, H₂SO₄ may be used instead of formic acid.

EXAMPLE 1

A culture medium (100 ml, pH 6.5) containing 1% of glucose 1% of dextrin, 0.5% of yeast extract, 0.5% of casein hydrolyzate, 0.1% of calcium carbonate and 1% of celite was dividedly poured in 500 ml Erlenmeyer flasks, which were autoclave-sterilized at 120° C. for 20 minutes. These media were inoculated with strains of one platinum loop taken from a slant culture medium of *Myceliophthora thermophila* M 4323 (FERM-BP No. 979) and were shaking cultured at 30° C. for 4 days. Thus obtained seed culture was transplanted to a 30 l jar fermenter containing 20 l of a culture medium (pH 6.5) containing 2% of glucose, 1% of peptone, 1% of CSL, 0.2% of potassium primary phosphate and 0.1% of magnesium sulfate which was previously sterilized and was cultured at 30° C. for 5 days under the condition of an aeration amount of 20 l/min, a rotation number of 200/min and an inner pressure of 0.8 atm. 20 l of thus obtained culture was filtered to obtain 18 l of a culture filtrate.

EXAMPLE 2

The culture filtrate (18 l) obtained in Example 1 was adjusted to pH 6.5 with 6N HCl, adsorbed to 1.5 l of carbon previously packed in a column. The column was well washed with about 10 l of water, then elution was effected with a 70% aqueous acetone solution and eluate was fractionated into fractions of 500 ml each. It was recognized that most of Estatin A and Estatin B having anti-papain activity were contained in fractions No. 3–10. These fractions No. 3–10 were concentrated under reduced pressure to about 500 ml and this was adsorbed to strongly acidic cation exchange resin Amberlite IR-120B (H⁺ type) 500 ml column. The column was well washed with about 3 l of water and elution was effected with a 1N aqueous ammonia and the eluate was fractionated into fractions of 200 ml each. Most of Estatin A and Estatin B exhibiting anti-papain activity were contained in fractions No. 7–No. 18. These fractions were concentrated under reduced pressure to about 50 ml and this was adjusted to pH 6.5. This concentrated liquid was submitted to strongly basic anion exchange resin Dowex ½ (Cl⁻ type) column of 400 ml and eluted with water and fractionated into fractions of 20 g each. Fractions Nos. 11–65 having anti-papain activity were concentrated under reduced pressure to obtain 620 mg of a crude substance.

EXAMPLE 3

The crude substance (620 mg) obtained in Example 2 was dissolved in 20 ml of a 30% methanol solution. To this solution was added 20 g of silica gel powder and they were well stirred and mixed, followed by removal of methanol and water under reduced pressure. Then, the mixture was poured on 300 ml of a silica gel column made of ethyl acetate:methanol:water (10:10:1) solvent and eluted with the same developing solvent and fractionated into fractions of 16 g each. Anti-papain activity was recognized in fraction Nos. 57–120 and Nos. 151–199. Fractions Nos. 57–120 were concentrated under reduced pressure to obtain 44.1 mg of crude crystal of Estatin A. Fractions Nos. 151–199 were concentrated under reduced pressure to obtain 26.7 mg of crude crystal of Estatin B.

EXAMPLE 4

The crude crystal of Estatin A (44.1 mg) obtained in Example 3 was dissolved in 10 ml of hot water. This solution was poured into a 1300 ml column of Sephadex G-15 and was eluted with water. The eluate was fractionated into fractions of 10 g each to find that most of Estatin A was eluted in fractions Nos. 79–87. These fractions were concentrated under reduced pressure to give a white needle crystal of Estatin A, which was collected on a glass filter and dried under reduced pressure to obtain 33 mg of a pure white needle crystal of Estatin A.

Similarly, 26.7 mg of the crude crystal of Estatin B obtained in Example 3 was dissolved in 10 ml of hot water, the resultant solution was poured into a column of 1300 ml of Sephadex G-15 and eluted with water. The eluate was fractionated into fractions of 10 g each. Most of Estatin B was eluted in fractions Nos. 90–101. These fractions were concentrated under reduced pressure to produce white needle crystal of Estatin B. This crystal was collected on a glass filter and dried under reduced pressure to obtain 18.3 mg of white needle crystal of pure Estatin B.

EXAMPLE 5

Synthesis of 1-nitroguanyl-3,5-dimethylpyrazole (2)

Nitroaminoguanidine (4.87 g) was dissolved in 93 ml of boiling water followed by addition of 0.94 ml of acetic acid and then added dropwise 4.87 ml of acetyl acetone. The mixture was stirred at 100° C. for 2 hours and allowed to cool. After the cooling, the resulting crystal (2) was filtered and recrystallized from ethanol-water.

4.78 g (yield 64%).
Mass (CI-isoBu) 184 (MH+).
Melting point 125°–126° C.
NMR (60 MHz, CDCl$_3$) 2.2 (s, 3H, CH$_3$), 2.6 (s, 3H, CH$_3$), 6.1 (br, 1H, =CH), 8–9 (br, 2H, NH×2).

EXAMPLE 6

Synthesis of N-carbobenzoxyl-N$^G$-nitroagmatine (3)

Commercially available CBZ-diaminobutane hydrochloride (1) (259 mg) and 201 mg of the compound (2) obtained in Example 5 (1.1 equivalent) were dissolved in 2.6 ml of ethanol and 140 μl (1 equivalent) of triethylamine was added to the solution and the mixture was refluxed with stirring for 3 hours. After having been left to cool, this was kept in a refrigerator overnight and resulting white crystal was filtered and washed with cold ethanol. Recrystallization from ethanol gave 144 mg of compound (3). Yield 47%.

Melting point 123°–124.5° C.
Mass (FAB) 310 (MH$^{30}$).
NMR (100 MHz, CDCl$_3$+DMSO-d$_6$) 1.57 (m, 4H, CH$_2$×2), 3.0–3.3 (m, 4H, CH$_2$×2), 5.07 (s, 2H, CH$_2$ph), 6.52 (br, 1H, NH), 7.33 (s, 5H, ph), 7.65 (br, 2H, NH$_2$).

EXAMPLE 7

Synthesis of N$^G$-nitroagmatine hydrobromide (4)

The compound (3) (112 mg) obtained in Example 6 was dissolved in 1 ml of a 25% HBr/acetic acid solution and the mixture was stirred at room temperature for 30 minutes. To this reaction mixture was added ether to give a precipitate and supernatant was decanted twice. The residue was recrystallized from methanol-ether and collected by filtration. The product was washed with cold methanol-ether to give a white solid.

81 mg (yield 88%). Melting point 173°–175° C.
Mass (FAB) 176 (MH+).
NMR (100 MHz, DMSO-d$_6$) 1.53 (m, 4H, CH$_2$×2) 2.6–3.0 (m, 2H, CH$_2$), 3.0–3.3 (m, 2H, CH$_2$), 7.72 (br, NH$_2$), 7.85 (br, NH$_2$), 7.0–8.0 (br, NH).

EXAMPLE 8

Synthesis of N-(BOC-L-phenylalanyl)-N$^G$-nitroagmatine (6a)

BOC-L-phe-OSu (5a) (707 mg) was dissolved in 6 ml of 1,2-dimethoxyethane. To this solution was added a solution of 500 mg of compound (4) obtained in Example 7 and 272 μl of triethylamine in 1 ml of water under cooling in an ice bath. This mixture was stirred at room temperature for 6 hours and concentrated under reduced pressure to a small volume. A 2.5% aqueous sodium carbonate solution was added to the residue and extraction with ethyl acetate was carried out three times. The combined ethyl acetate layer was washed with 1M-citric acid and then brine, and was passed through Whatman 1 PS paper filter and the filtrate was concentrated under reduced pressure. The residue was purified by a silica gel column chromatography (CHCl$_3$:CH$_3$OH= from 40:1 to 20:1). The eluate was concentrated under reduced pressure to afford 710 mg of white foam. (Yield 86%)

Mass (FAB) 423 (MH+).
NMR (60 MHz, CDCl$_3$) 1.3–1.6 (m, 13H, C(CH$_3$)$_3$, CH$_2$×2), 2.8–3.5 (m, 6H, phCH$_2$, (CH$_2$)×2), 4.5 (m, 1H, CH), 5.6 (br 1H, NH), 7.2 (s, 5H, ph), 6.8–7.1, 7.5–8.5 (br, respectively, 3H, NH×3).

EXAMPLE 9

Synthesis of N-(O-benzyl-BOC-L-tyrosyl)-N$^G$-nitroagmatine (6b)

BOC-O-benzyl-tyrosyl-OSu (915 mg) was dissolved in 9 ml of 1,2-dimethoxyethane. To this solution was added a solution of 500 mg of nitroagmatine.HBr and triethylamine (272 μl) in water (1 ml) under cooling in an ice bath, and the mixture was stirred at room temperature overnight (15 hours). After concentration to a small volume under reduced pressure, 2.5% aqueous sodium carbonate solution was added to the residue and was extracted with ethyl acetate three times. The combined ethyl acetate layer was washed with 1M-citric acid and then with brine, passed through Whatman 1 PS paper filter and the filtrate was concentrated under reduced pressure. The residue was purified by a silica gel column chromathography (CHCl$_3$:CH$_3$OH=from 40:1 to 20:1) and the eluate was concentrated under reduced pressure to give 922 mg of a white foam (Yield 89%).

Mass (FAB) 529 (MH+).
NMR (100 MHz, CDCl$_3$), 1.38 (s, 9H, (CH$_3$)$_3$), 1.49, 1.79 (m, respectively, 2H, 2H, (CH$_2$)×2), 2.95 (d, 2H, phCH$_2$), 2.1–2.4 (m, 4H, CH$_2$×2), 4.28 (sextet, 1H, CH), 5.02 (s, 2H, CH$_2$ of O-benzyl), 5.20 (d, 1H, NH), 6.43 (t, 1H, NH), 6.92 (ABq, 4H, CH$_2$phOH), 7.38 (m, 5H, ph), 7.56 (br, 2H, NH$_2$), 8.0–8.5 (br, 1H, NH).

EXAMPLE 10

Synthesis of N-L-phenylalanyl-N$^G$-nitroagmatine (7a)

The compound (6a) (200 mg) obtained in Example 8 was dissolved in 2 ml of 99% formic acid and this solution was stirred at room temperature for 4 hours. The mixture was concentrated under reduced pressure below 30° C. and the residue was charged on Dowex 50 (H+), washed with water until neutral, the eluted with NH$_4$OH/ethanol and concentration of the eluate under reduced pressure gave 154 mg (quantitative) of glassy substance.

Mass (FAB) 323 (MH+).
NMR (100 MHz, DMSO-d$_6$), 1.38 (m, 4H, CH$_2$×2) 2.6–3.4 (m, 7H, CH$_2$×2, CH$_2$, CH), 7.21 (s, 5H, ph), 7.8 (br, 5H, NH, NH$_2$).

EXAMPLE 11

Synthesis of N-L-(O-benzyl)-tyrosyl-N$^G$-nitroagmatine (7b)

The compound (6b) (900 mg) obtained in Example 9 was dissolved in 15 ml of 99% formic acid and this solution was stirred at room temperature for 2 hours. After concentration under reduced pressure below 30° C., ethanol-methanol was added to the residue and this was concentrated again under reduced pressure. The residue was dissolved in water and this solution was made alkaline with N-NaOH and extracted with chloroform serveral times. The chloroform layer was washed with water, then passed through Whatman 1 PS paper filter and concentrated under redueced pressure to obtain 0.61 g of a glassy substance (yield 84%).

Mass (FAB) 429 (MH+).

NMR (100 MHz, CDCl₃) 1.52 (m, 4H, CH₂×2), 2.55 (dd, 1H, CH), 3.0–3.7 (m, 6H, CH₂×2, phCH₂), 5.03 (s, 2H, OCH₂ph), 6.90 (ABq, 4H, Obzyl), 7.90 (m, 5H, ph), 7.6 (br, NH₂, NH), 8.4 (br, NH).

EXAMPLE 12

Synthesis of N-[N-(D- and L-3-transethoxycarbonyloxiran-2-carbonyl)-L-phenylalanyl]-N$^G$-nitroagmatine (9a)

The compound (7a) (320 mg) obtained in Example 10 and 180 mg of DL-ethyl hydrogen trans-epoxy-succinate were dissolved in 4 ml of dimethylformamide. Under ice cooling, to the resulting solution were added 200 μl of diethylphosphorocyanidate and 180 μl of triethylamine, followed by stirring at room temperature for 4 hours. The solution was diluted with ethyl acetate and washed with N-HCl, saturated NaHCO₃ and brine in turn. The ethyl acetate layer was dried over MgSO₄ and concentrated under reduced pressure to give a crystal, which was collected by filtration and washed with ether. 310 mg (yield 67%)

Mass (FAB) 465 (MH³⁰).

NMR (100 MHz, CDCl₃+DMSO-d₆) 1.2–1.6 (m, 7H, CH₂×2, COOCH₂CH₃), 2.9–3.3 (m, 6H, CH₂×2, phCH₂), 3.56 (dd×2, 2H,

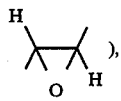

4.17 (q×2, 2H, COOCH₂CH₃), 4.60 (dd, 1H, CH), 7.24 (s, 5H, ph), 7.2–7.6 (br, NH, NH₂).

EXAMPLE 13

Synthesis of N-[N-(D- and L-3-trans-carboxyoxiran-2-carbonyl)-L-phenylalanyl]-N$^G$-nitroagmatine (10a)

The compound (9a) (51 mg) obtained in Example 12 was dissolved in 1 ml of methanol and 53 μl (1 equivalent) of 2N-aqueous KOH solution was added thereto under ice cooling. The mixture was stirred at room temperature for 3 hours, diluted with water, charged on Dowex 50 (H+) eluted with H₂O-ethanol. The fractions which were acidic on pH test paper and absorbed ultraviolet ray were collectd and concentrated under reduced pressure. To the residue was added ether and this was collected by filtration to obtain 47 mg (quantitative) of colorless powder.

Mass (FAB) 437 (MH+).

NMR (100 MHz, DMSO-d₆), 1.2–1.5 (m, 4H, CH₂×2), 2.8–3.2 (m, 6H, CH₂×2, ph.CH₂), 3.32 (d, 1H, 3.60 (d, 1H,

4.48 (br, q, 1H, CH), 7.24 (s, 5H, ph), 7.5–8.6 (br, NH, NH₂).

EXAMPLE 14

Synthesis of N-[N-(D- and L-3-trans-carboxyoxiran-2-carbonyl-L-phenylalanyl-]agmatine (Ia) [=Estatin A whose epoxy portion is in DL-form]

The compound (10a) (1.0 g) obtained in Example 13 was dissolved in 4 ml of acetic acid and 3 ml of H₂O, followed by adding a catalytic amount of palladium on carbon (10%, purchased from Engelhard Industries Co., Ltd.) and then 40 ml of methanol. The solution was stirred vigorously at room temperature in a hydrogen atmosphere. After 6 hours, the catalyst was filtered off and the filtrate was concentrated under reduced pressure. The residue was dissolved in water, charged in active carbon column (25–30 ml) and then washed with water. Upon recognition of neutral eluate, elution with 50% aqueous acetone solution was carried out. Fractions positive in Sakaguchi reaction were collected and concentrated under reduced pressure to obtain a crystal, which was recrystallized from ethanol-water 0.274 mg (yield 31%). Further synthesis was carried out to obtain about 6 g of the titled compound.

IR: As shown in FIG. 5 (KBR method).

NMR (100 MHz, D₂O-DCl), 1.1–1.4 (m, 4H, CH₂×2), 2.8–3.1 (m, 6H, CH₂×2, phCH₂), 3.52 (d, H,

3.67 (d, 1H,

4.46 (t, 1H, CH), 7.25 (s, 5H, ph)

EXAMPLE 15

Synthesis of N-[N-(L-3-trans-ethoxycarbonyloxiran-2-carbonyl)-L-phenylalanyl]-N$^G$-nitroagmatine (9a)

The compound (7a) (13.97 g) obtained in Example 10 and 7.64 g of L-ethyl hydrogen trans-epoxysuccinate was dissolved in 150 ml of dimethylformamide, followed by addition of 8.55 ml of diethylphoshorocyanidate. This solution was ice-cooled and thereto was added dropwise 7.86 ml of triethylamine. Then, the solution was stirred at room temperature for 4 hours. The reaction mixture was diluted with ethyl acetate and washed with N—HCL, saturated aqueous NaHCO₃, and brine in turn. The organic layer was dried over MgSO₄ and then concentrated under reduced pressure. The residue was crystallized from ethyl acetate. 15.28 g (yield 76%).

[α]$_D^{24}$+48.00° (C 0.502, methanol).

Mass (FAB) m/e 465 (MH+).

NMR (CDCl$_3$+DMSO-d$_6$), $\delta_{ppm}^{TMS}$ 1.29 (t, 3H, COOCH$_2$CH$_3$), 1.2–1.6 (m, 4H, CH$_2$×2), 2.9–3.3 (m, 6H, CH$_2$×2, phCH$_2$), 3.32 (d, 1H, J=1.7 Hz,

3.65 (d, 1H, J=1.7 Hz,

4.21 (q, 2H, COOCH$_2$CH$_3$), 4.60 (br, dd, 1H, CH) 7.22 (s, 5H, ph), 7.6–8.4 (br, 5H, NH, NH$_2$).

EXAMPLE 16

Synthesis of O-benzyl-N-[N-(L-3-trans-ethoxycarbonyloxiran-2-carbonyl)-L-tyrosyl]-N$^G$-nitroagmatine (9b)

The compound (7b) (7.0 g) obtained in Example 11, 2.87 g of L-ethyl hydrogen trans-epoxysuccinate and 3.03 ml of diethylphoshorocyanidate were dissolved in 70 ml of dimethylformamide and to the solution was added dropwise 2.50 ml of triethylamine. The mixture was subjected to after-treatments in the same manner as in Example 15, eluted with CHCl$_3$:CH$_3$OH=50:1 and purified by silica gel column chromatography. 7.60 g (foam; yield 82%)

[α]$_D^{24}$+45.44° (C 1.12, methanol).

Mass (FAB) m/e 571 (MH+).

NMR (CDCl$_3$) $\delta_{ppm}^{TMS}$, 1.26 (t, 3H, COOCH$_2$CH$_3$), 1.2–1.6 (m, 4H, CH$_2$×2), 2.9–3.3 (m, 7H, phCH$_2$, CH$_2$×2,

3.66 (d, 1H,

4.16 (q, 2H, COOCH$_2$CH$_3$), 4.66 (br, q, 1H, CH), 5.00 (s, 2H, OCH$_2$ph), 6.92 (ABq, 4H, aromatic) 7.36 (s, 5H, ph), 7.0–8.5 (br, NH, NH$_2$).

EXAMPLE 17

Synthesis of N-[N(L-3-trans-carboxyoxiran-2-carbonyl)-L-phenylalanyl]-N$^G$-nitroagmatine (10a)

The compound (9a) (14.0 g) obtained in Example 15 was dissolved in 280 ml of methanol and to the solution was added under ice cooling dropwise 15.2 ml of 2N-KOH. The solution was stirred at room temperature for 3 hours and then diluted with addition of 80 ml of water. This solution was charged on Dowex 50 (H+) and eluted with H$_2$O-ethanol (about 50%). The eluate was concentrated under reduced pressure and the residue was crystallized from ethanol-ethylacetate.

12.11 g (yield 92%).

Mass (FAB) m/e 437 (MH+).

NMR (DMSO-d$_6$), $\delta_{ppm}^{TMS}$, 1.2–1.5 (m, 4H, CH$_2$×2), 2.8–3.2 (m, 6H, phCH$_2$, CH$_2$×2), 3.32 (d, 1H,

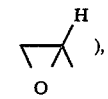

3.60 (d, 1H,

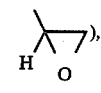

4.48 (br, q, 1H, CH), 7.24 (s, 5H, ph), 7.5–8.6 (br, NH, NH$_2$)

EXAMPLE 18

Synthesis of O-benzyl-N-[N-(L-3-trans-carboxyoxiran-2-carbonyl)-L-tyrosyl]-N$^G$-nitroagmatine (10b)

The compound (9b) (0.687 g) obtained in Example 16 was dissolved in 12 ml of methanol and to the solution was added under ice cooling dropwise 0.6 ml of 2N-KOH. The solution was stirred at room temperature for 3 hours and thereafter was rendered acidity with 50% acetic acid. Teh resultant precipitate was collected by filtration and washed with water to obtain a gel-like substance. 0.45 g (yield 70%)

Mass (FAB) m/e 498 (MH+-45).

NMR (DMSO-d$_6$), $\delta_{ppm}^{TMS}$, 1.2–1.6 (m, 4H, CH$_2$×2), 2.7–3.2 (m, 6H, phCH$_2$, CH$_2$×2), 3.32 (d, 1H,

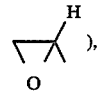

3.60 (d, 1H,

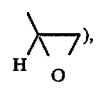

4.42 (br, q, 1H, CH), 5.05 (s, 2H, OCH$_2$ph), 7.00 (ABq, 4H, aromatic), 7.40 (m, 5H, ph), 7.8–8.6 (br, NH, NH$_2$).

EXAMPLE 19

Synthesis of N-[N-(L-3-trans-carboxyoxiran-2-carbonyl)-L-phenylalanyl]agmatine (Ia)

The compound (10a) (11.28 g) obtained in Example 17 was dissolved in a mixed liquid of 1600 ml of methanol, 160 ml of acetic acid and 120 ml of water and 10% palladium on carbon was added to the solution. The solution was stirred at room temperature in a hydrogen atmosphere overnight. The catalyst was filtered off and the filtrate was concentrated under reduced pressure. The residue was dissolved in water, charged on about 250 ml of an active carbon (WAKO) for chromatography, washed with water until neutral and then eluted with 50% aqueous acetone. The eluate was concentrated under reduced pressure to obtain a crystal.

6.22 g (yield 62%).

$[\alpha]_D^{24} +47.37°$ (C 0.61, H$_2$O).

IR: Identified with the absorption peak as shown in FIG. 3.

Mass (FAB) m/e 392 (MH+).

NMR (D$_2$O-DCl), $\delta_{ppm}^{TMS}$, 1.1–1.3 (m, 4H, CH$_2$×2), 2.8–3.1 (m, 6H, phCH$_2$, CH$_2$×2), 3.35 (d, 1H,

), 3.60 (d, 1H,

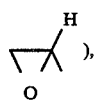), 4.44 (t, 1H, CH), 7.0–7.3 (m, 5H, ph).

EXAMPLE 20

Synthesis of N-[N-(L-3-trans-carboxyoxiran-2-carbonyl)-L-tyrosyl-]agmatine [Ic] Estatin B The compound (10b) (5.28 g) obtained in Example 18 dissolved in 700 ml of acetic acid:water:methanol (2:1.5:20) and the solution was hydrogenated with 10% palladium on carbon and stirred for 15 hours. The catalyst was filtered off and the filtrate was repeatedly extracted with hot water-ethanol.

1.12 g (yield 31%).

$[\alpha]_D^{24} +45.25°$ (C 0.137, 0.1N HCl).

IR: Corresponded to the absorption peak as shown in FIG. 4.

Mass (FAB) m/e 408 (MH+).

NMR (D$_2$O-DCl), $\delta_{ppm}^{TMS}$, 1.2–1.4 (m, 4H, CH$_2$×2), 2.9–3.2 (m, 6H, CH$_2$×2, HOphCH$_2$), 3.48 (d, 1H,

), 3.74 (d, 1H,

), 4.51 (t, 1H, CH), 6.96 (ABq, 4H, aromatic).

We claim:

1. A compound represented by the formula [I]:

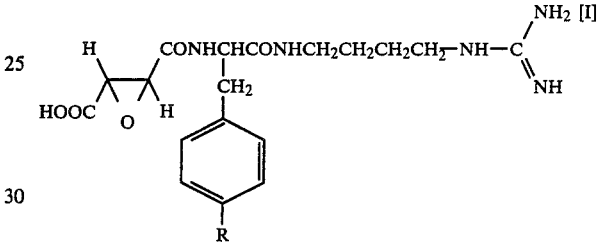

wherein R represents a hydrogen atom or a hydroxyl group, a pharmaceutically acceptable salt or a hydrate thereof.

2. A composition having enzyme inhibitory activity which contains an effective amount of the compound of claim 1.

* * * * *